(12) United States Patent
Devaux et al.

(10) Patent No.: US 7,790,171 B1
(45) Date of Patent: Sep. 7, 2010

(54) ANTIVIRAL PEPTIDES OBTAINED FROM THE TRYPTOPHAN-RICH HYDROPHOBIC CLUSTER OF THE HIV-1 REVERSE TRANSCRIPTASE

(75) Inventors: Christian Devaux, Montpellier (FR); Véronique Hebmann, Saint Bauzille de Montmel (FR); Gilles Divita, Villeurbanne (FR); Frédéric Heitz, Grabels (FR); Catherine May Morris, San Diego, CA (US); Jean Mery, Saint Gely du Fesc (FR); Roger S. Goody, Dortmund (DE)

(73) Assignee: Centre National de la Recherche Scientifique (C.N.R.S.), Paris (FR)

( * ) Notice: Subject to any disclaimer, the term of this patent is extended or adjusted under 35 U.S.C. 154(b) by 2358 days.

(21) Appl. No.: 09/648,557

(22) Filed: Aug. 25, 2000

(51) Int. Cl.
A61K 39/21 (2006.01)
A61K 39/00 (2006.01)
A61K 38/04 (2006.01)
(52) U.S. Cl. ............... 424/188.1; 424/208.1; 424/192.1; 530/328
(58) Field of Classification Search ................ 435/5; 424/188.1, 208.1
See application file for complete search history.

(56) References Cited

U.S. PATENT DOCUMENTS 5,464,933 A * 11/1995 Bolognesi et al. ........... 530/324

FOREIGN PATENT DOCUMENTS

WO WO 01/24810 4/2001
WO WO 02/10201 2/2002

OTHER PUBLICATIONS

Morris, M. C., et al., 1999, A new potent HIV-1 reverse transcriptase inhibitor, J. Biol. Chem. 274(35):24941-24946.*
Korber, B., et al., 1998, Human retroviruses and AIDS. A compilation and analysis of nucleic acid and amino acid sequences, Los Alamos National Laboratory, Los Alamos, New Mexico.*
van der Burg, S. H., et al., 1997, HIV-1 reverse transcriptase-specific CTL against conserved epitopes do not protect against progression to AIDS, J. Immunol. 159:3648-3654.*
Divita, G., et al., 1995, Interface peptides as structure-based human immunodeficiency virus reverse transcriptase inhibitors, J. Biol. Chem. 270(48):28642-28646.*
Morris, M. C., et al., 1997, A new peptide vector for efficient delivery of oligonucleotides into mammalian cells, Nuc. Acids Res. 25(14):2730-2736.*
Divita et al., J. of Biol. Chem., 269:18:13080-13083, 1994.
Divita et al., J. of Biol. Chem., 270:48:28642-28646, 1995.
Divita et al., J. Mol. Biol. 245:508-521, 1995.
Morris et al., Nucleic Acids Research, 25:14:2730-2736, 1997.
Morris et al., J. of Biol. Chem., 274:35:24941-24946, 1999.
Restle et al., J. Biol. Chem., 265:16:8986-8988, 1990.
Van Der Burg et al., "HIV-1 Reverse Transcriptase-Specific CTL Against Conserved Epitopes Do Not Protect Against Progression to AIDS", The Journal of Immunology, 1997, 159: pp. 3648-3654.

* cited by examiner

*Primary Examiner*—Jeffrey S. Parkin
(74) *Attorney, Agent, or Firm*—Buchanan Ingersoll & Rooney PC

(57) ABSTRACT

The invention is drawn to a novel class of drugs directed against HIV, comprising a peptide or analog comprising a decapeptide, said decapeptide containing (from N-terminus to the C-terminus) a basic amino acid in position 1, an acidic amino acid in positions 2 and 5, and a tryptophan in positions 4, 7, and 8, and to a method of treatment of HIV infections, in particular multidrug-resistant HIV infections.

21 Claims, 8 Drawing Sheets

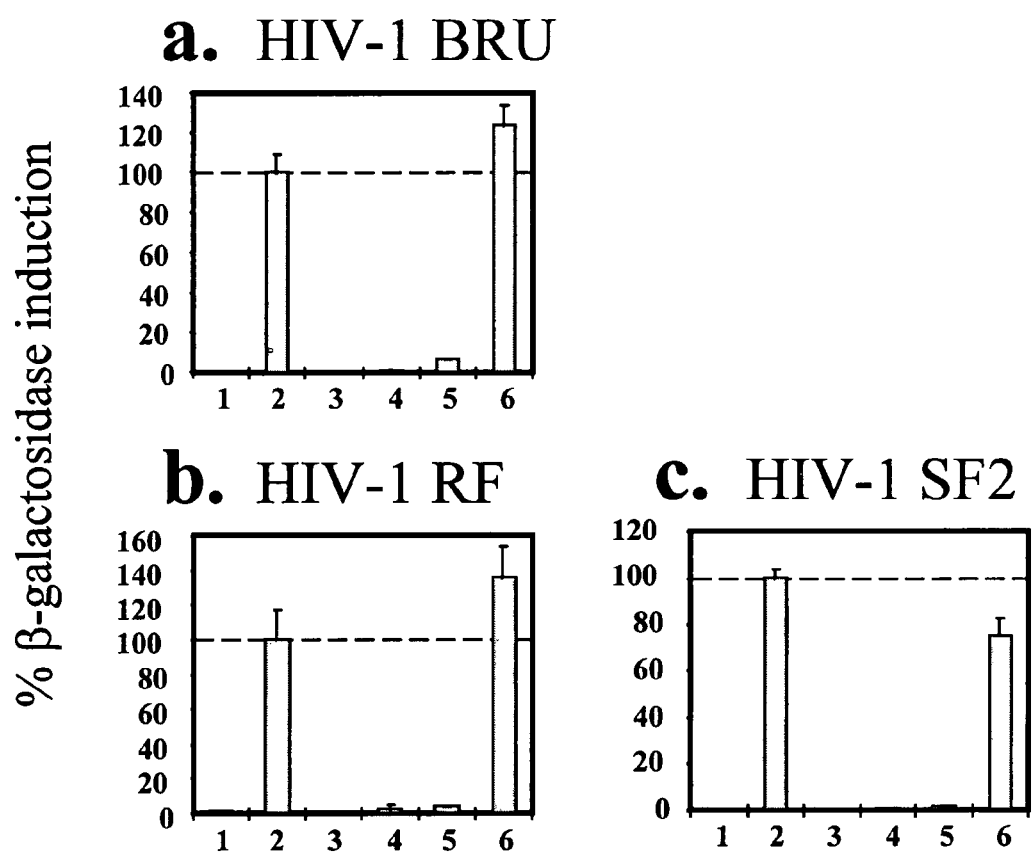
FIG 2.A

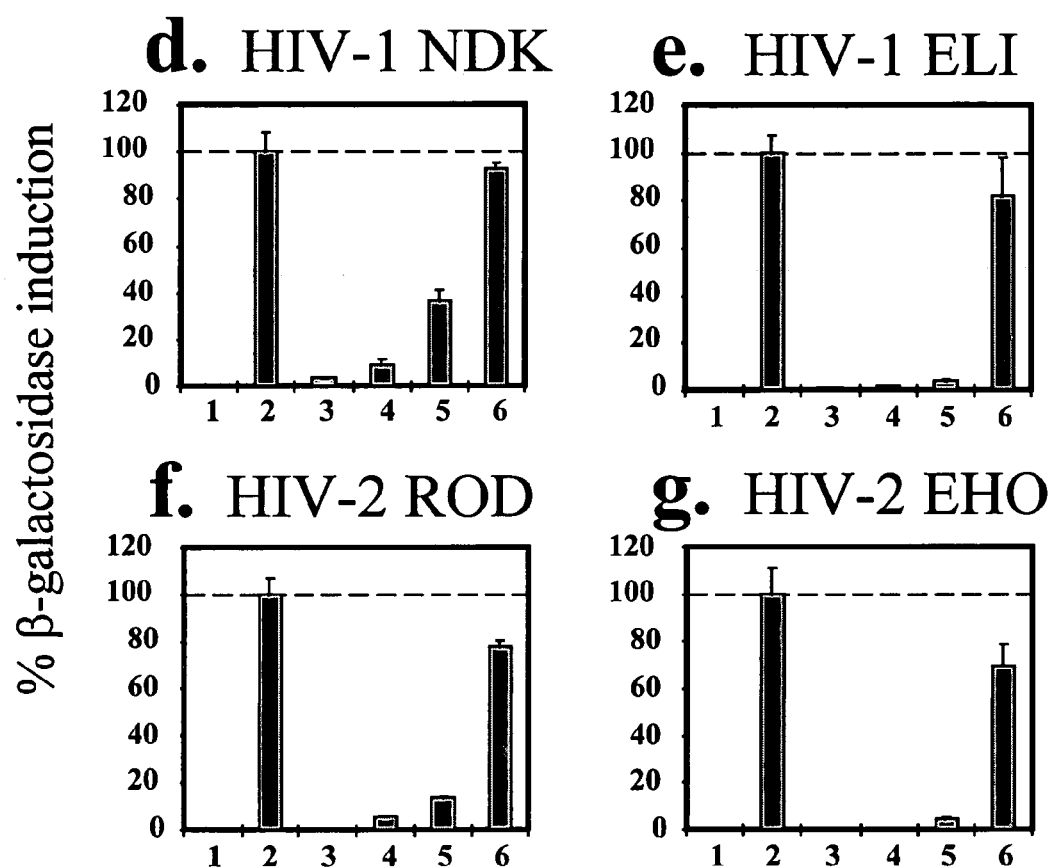
FIG 2.B

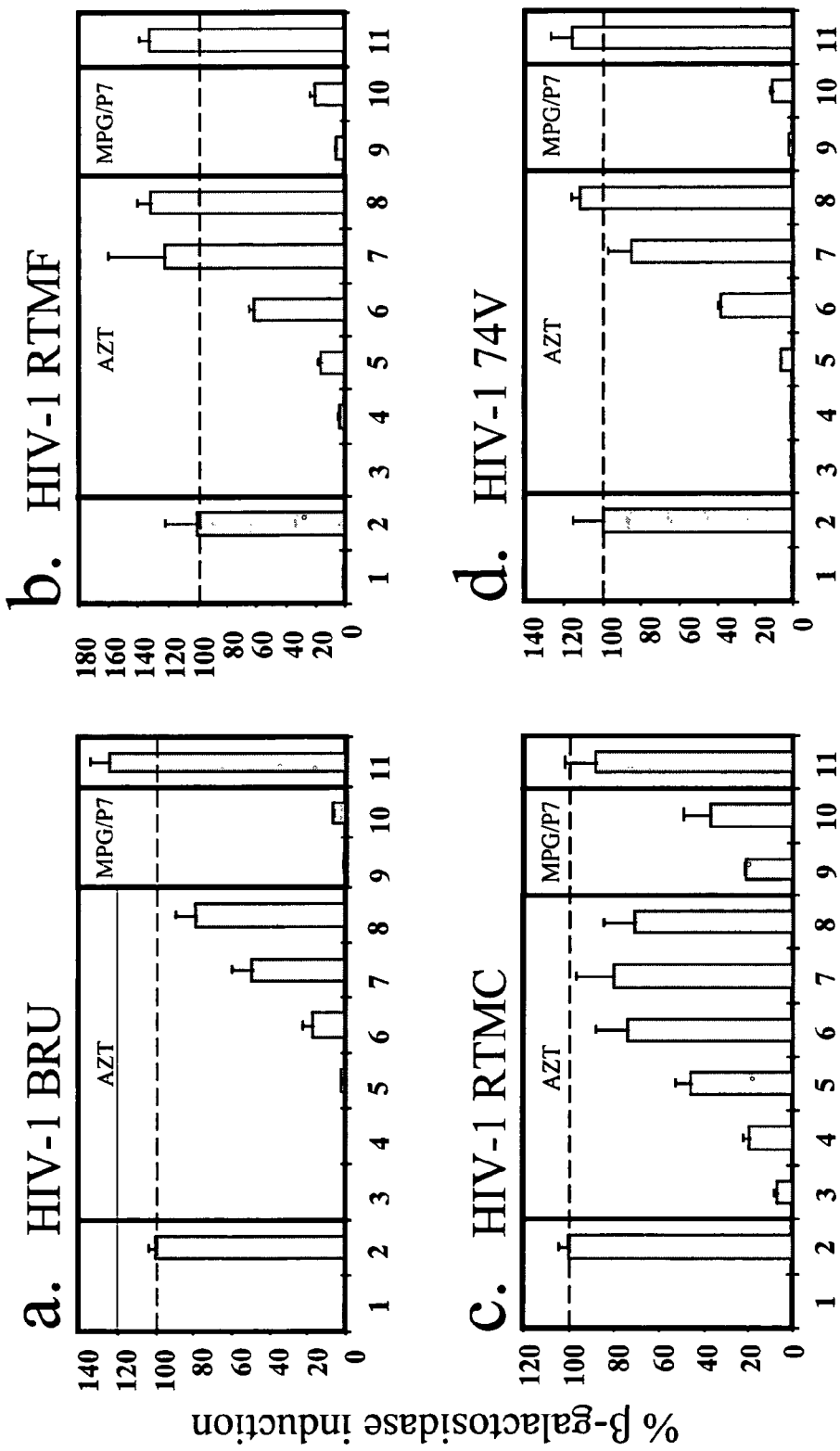
FIG. 3.A

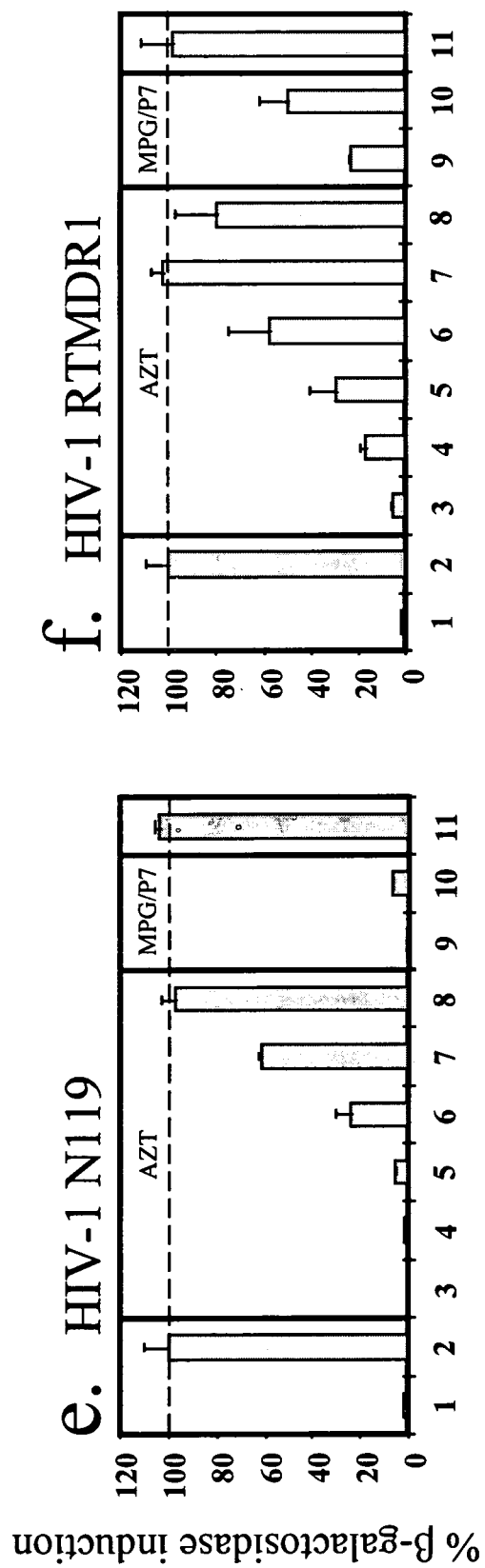
FIG. 3.B

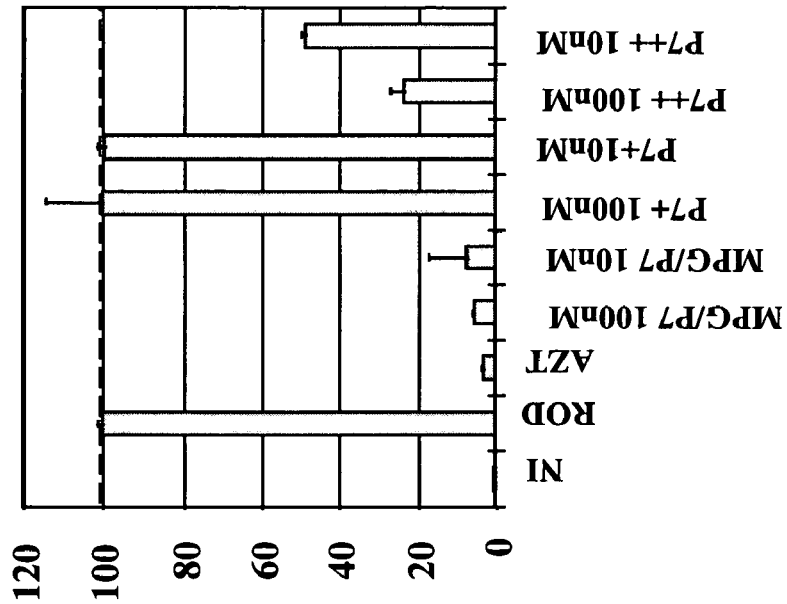
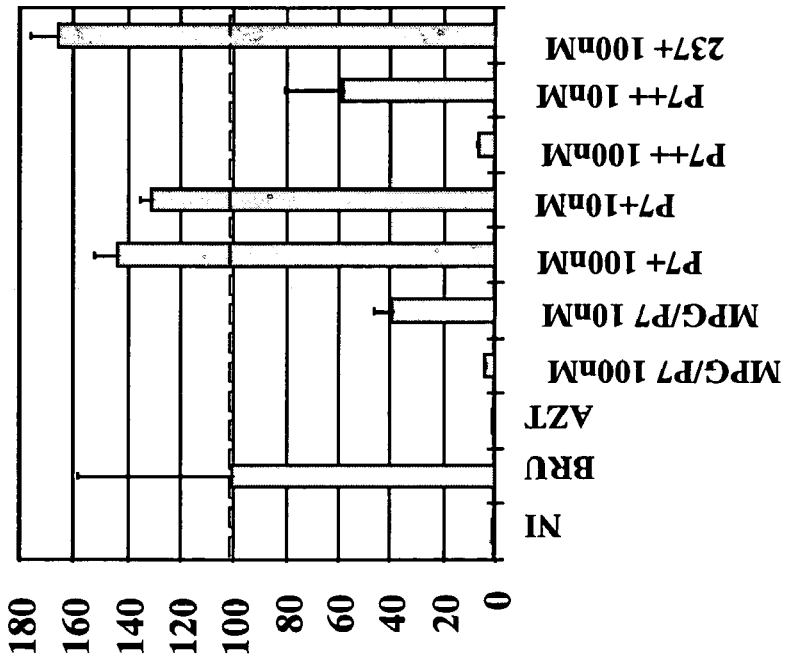
FIG. 4.A

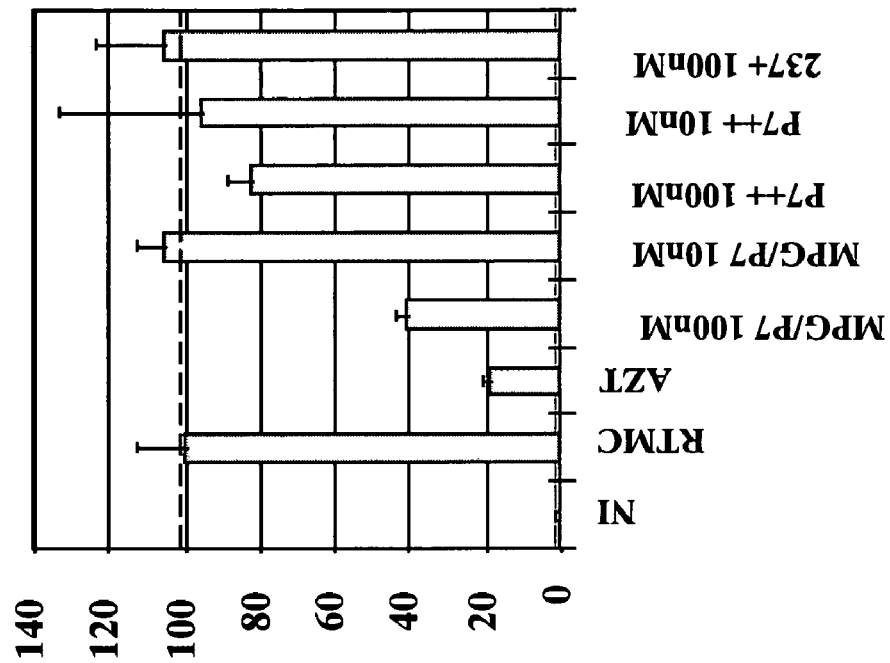
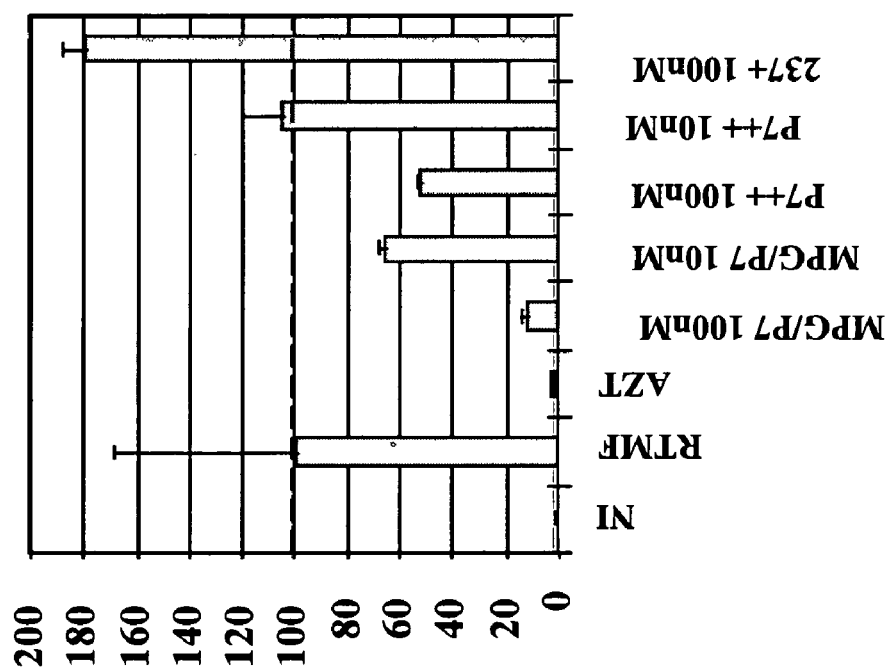
FIG. 4.B

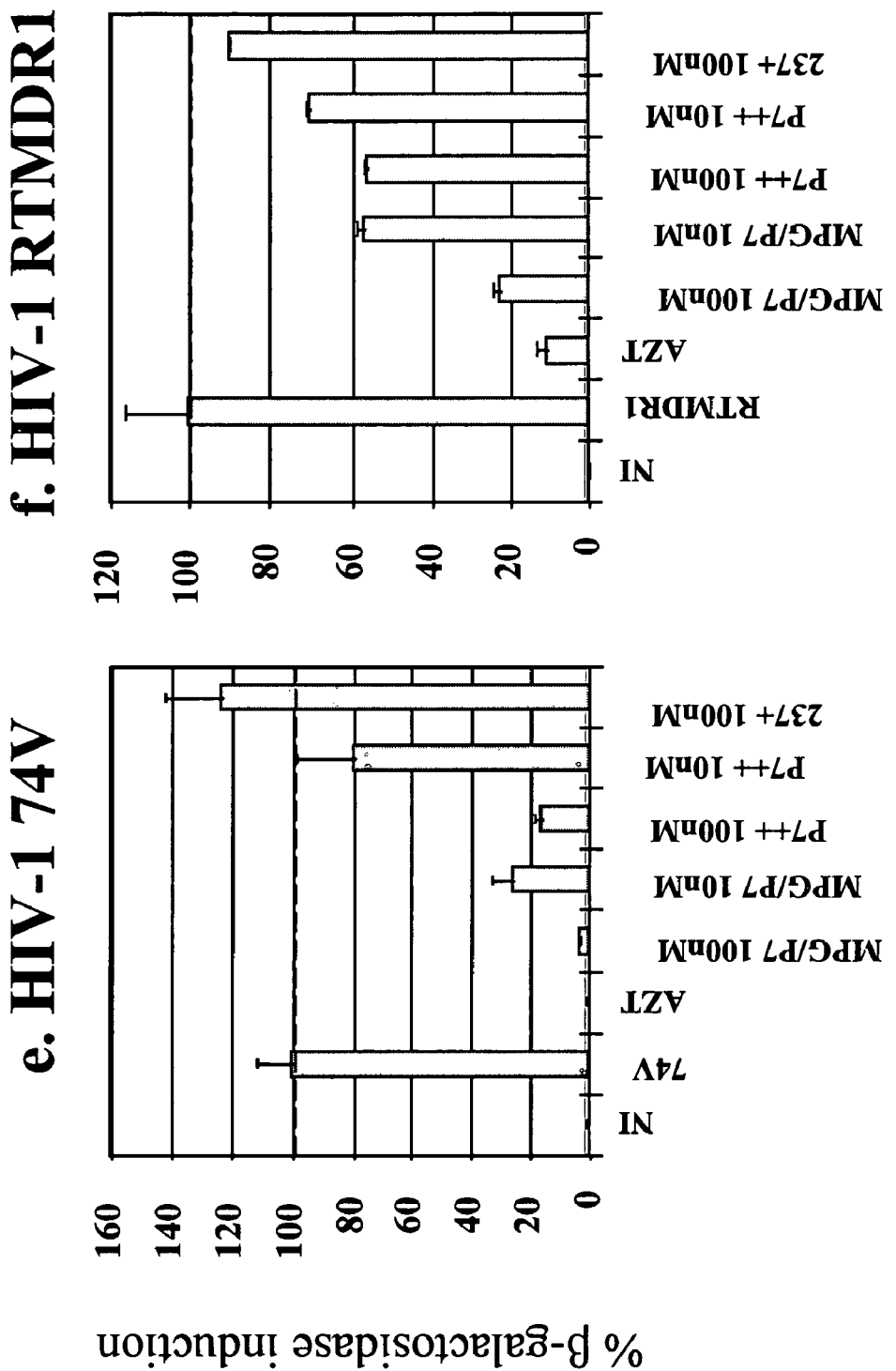
FIG. 4.C

ANTIVIRAL PEPTIDES OBTAINED FROM THE TRYPTOPHAN-RICH HYDROPHOBIC CLUSTER OF THE HIV-1 REVERSE TRANSCRIPTASE

FIELD OF THE INVENTION

The invention is drawn to a novel class of drugs directed against HIV, inhibiting the dimerization of reverse transcriptase of the virus, and to a method of treatment of HIV infections, in particular multidrug-resistant HIV infections.

BACKGROUND OF THE INVENTION

In the last decade, a number of molecules have become available for the treatment of HIV-infected individuals. Therapeutic regimens based on the combination of reverse transcriptase inhibitors and protease inhibitors have been shown to reduce plasma HIV-1 RNA to undetectable levels in patients, increase CD4 cell counts and delay progression toward AIDS.

HIV reverse transcriptase (RT) inhibitors that target the polymerase activity of RT, can be subdivided into two classes of potent agents: nucleosides that terminate viral DNA synthesis, such as zidovudine (AZT), dideoxyinosine (ddI) and dideoxycytidine (ddC), and nonnucleoside analogs that bind to a hydrophobic cavity adjacent to the polymerase active site such as nevapirine (1). However, these agents present several limitations, including toxicity which sometimes requires patient's treatment to be suspended (2), and the emergence of resistant strains which are generated through the exceptionally high rate of mutagenesis of RNA viruses (3-6). For example, resistance to zidovudine is conferred by amino acid changes that appear in an orderly fashion: a K70R mutation first, followed by T125F/Y, M41L, D67N, and 1(219Q mutations (7,8). Similarly, other mutations correlate with resistant phenotype to other RT inhibitors (9). Thus, the development of novel compounds that are active against multidrug-resistant HIV variants is urgently needed.

An interesting feature of HIV-1 RT is that the dimeric form of the enzyme consisting of two polypeptides p66 and p51, is absolutely required for its catalytic activities (10). Based on the x-ray crystallographic structure of HIV-1 RT, it was previously demonstrated that the first interaction between p66 and p51 occurs in a Tryptophan (Trp)-rich hydrophobic cluster located in the connection subdomain of the two subunits and is followed by a conformational change involving the thumb and the finger subdomains of p51 as well as the RNase-H and the palm subdomains of p66 (11).

SUMMARY OF THE INVENTION

The present invention is based on the concept that the dimerization process of RT could be an interesting target for AIDS chemotherapy, and on the description of new inhibitors of HIV replication, based on the inhibition of RT dimerization. These inhibitors comprise peptides that will interact with the conserved motif necessary for dimerization of the p51 and p66 subunit of the HIV-RT.

Based on the concept that a small ligand of the connection subdomains could inhibit RT dimerization, a short 10-residue synthetic peptide (p7) derived from the Trp-rich cluster at the interface of the connection subdomains of the p66 and p51 (KETWETWWTE; residues 395-404 of HIV-1 $BH_{10}RT$, SEQ ID NO:1) was designed. This peptide p7 is a powerful inhibitor of HIV-1 RI dimerization in vitro and abolishes the production of viral particles in HIV-1 BRU-infected cultured CEM cells at a concentration of $10^{-7}$ M, or $10^{-8}$ M when complexed with the carrier peptidyl system MPG previously shown to improves the delivery of molecules into cells (14 and 15, both incorporated herein by reference in their totality). Interestingly, p7 does not exhibit any toxicity in CEM cells at concentrations below $10^{-5}$ M. These encouraging studies prompted to pursue the characterization of this compound as a model for potential new antiviral drugs.

The present application demonstrates the potency of the MPG/p7 complex in the abolition of the production of HIV-1 and HIV-2 viruses and demonstrates that MPG/p7 is also a potent inhibitor of drug resistant adapted HIV-1 strains.

DESCRIPTION OF THE FIGURES

FIG. 2: Effect of MPG/p7 (SEQ ID NO:1) on replication of different subtypes of HIV-1 and HIV-2 studied using MAGIC5 cells. MAGIC-5 cells were incubated with 50 µl of stock HIV preparation corresponding to 1000×$TCID_{50}$/ml. a, HIV-1 BRU; b, HIV-1 RF; c, HIV-1 SF2 (FIG. 2.A); d, HIV-1 NDK; e, HIV-1 ELI; f, HIV-2 ROD; g, HIV-2 EHO (FIG. 2.B) in medium alone (lane 2), medium supplemented with AZT ($10^{-5}$ M) (lane 3), MPG/p7 at $10^{-7}$ and $10^{-8}$ M (lane 4 and 5 respectively), or MPG/p237 (SEQ ID NO:5) at $10^{-6}$ M (lane 6) additive. After 3 days in culture, 13-gal activity was evaluated in cell lysates by measuring absorbance at 410 nm. β-gal activity in uninfected MAGIC5 cells was measured as control (lane 1). All results have been normalized with respect to β-gal activity induced by each virus (100% induction). The calculated values represent means of duplicate. Each figure is representative of at least three independent experiments.

FIG. 3: Effect of MPG/p7 (SEQ ID NO:1) on replication of reference escape variant viruses. MAGIC-5 cells were incubated with 50 µl of stock HIV preparation corresponding to 1000×$TCID_{50}$/ml of a, HIV-1 BRU; b, HIV-1 RTMF; c, HIV-1 RTMC; d, HIV-1 74V (FIG. 3.A); e, HIV-1 N119; f, HIV-1 RTMDR1 (FIG. 3.B), in medium alone (lane 2) or medium supplemented with AZT at $10^{-5}$ M, $10^{-6}$ M, $10^{-7}$ M, $10^{-8}$ M, $10^{-9}$ M, and $10^{-10}$ M (lanes 3 to 8 respectively), MPG/p7 at $10^{-8}$ and $10^{-7}$M (lanes 9 and 10), or MPG/p237 at $10^{-6}$M (lane 11) additive. β-gal activity was evaluated on day 3 after virus exposure. β-gal activity in uninfected MAGIC5 cells was measured as control (lane 1). All results have been normalized (see legend of FIG. 2). The calculated values represent means of duplicate. Each figure is representative of at least three independent experiments.

FIG. 4: Effect of MPG/p7 (SEQ ID NO:1), peptide p'7+ (SEQ ID NO:6) and peptide p7++ (SEQ ID NO:7) on replication of reference viruses. MAGIC-5 cells were incubated with 50 µl of stock HIV preparation corresponding to 1000× $TCID_{50}$/ml of a, HIV-1 BRU; b, HIV-2 ROD (FIG. 4.A); c, HIV-1 RTMF; d, HIV-1 RTMC (FIG. 4. B); e, HIV-174V; f HIV-1 RTMDR1 (FIG. 4.C). NI: non infected; BRU: infected by virus BRU without inhibitor (or other viruses in other panels); AZT: medium supplemented with AZT at $10^{-5}$ M; MPG/p7: medium supplemented with MPG/p7 at the indicated concentration; p7+: medium supplemented with p7+ at the indicated concentration; p7++: medium supplemented with p7++ at the indicated concentration; 237+: medium supplemented with MPG/237 (SEQ ID NO:5) at the indicated concentration; β-gal activity was evaluated on day 3 after virus exposure. All results have been normalized (see legend of FIG. 2). The calculated values represent means of duplicate. Each figure is representative of at least three independent experiments.

DESCRIPTION OF THE PREFERRED EMBODIMENTS

Figure 1:
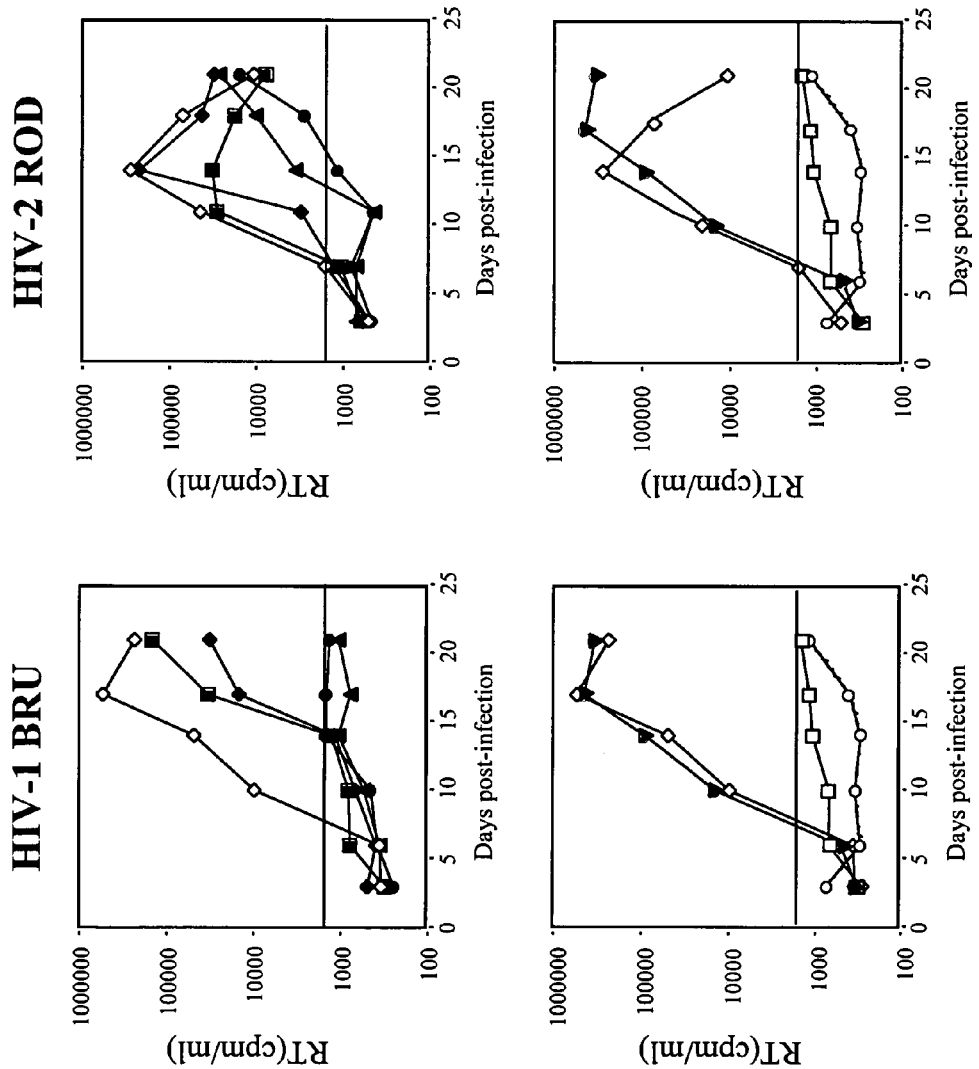
FIG. 1: Effect of different concentrations of MPG/p7 (SEQ ID NO:1) on HIV-1 and HIV-2 in CEM cell cultures. CEM cells exposed to 100 µl of viral suspensions containing 1000× 50% tissue culture infective dose ($TCID_{50}$)/ml of HIV-1 BRU (left panels) or HIV-2 ROD (right panels). a, HIV-infected cells were cultured in medium alone (white diamonds) or medium supplemented with MPG/p7 at $10^{-7}$ M (black circles), $10^{-8}$ M, (black up triangles), $10^{-9}$ M (black diamonds), and $10^{-10}$ M (black squares). b, As controls, HIV-infected cells were treated with either azidothymidine (AZT: $10^{-5}$ M) (white squares) or peptide MPG/p237 (SEQ ID NO:5) at $10^{-6}$ M (black down triangles). Viral production was monitored by measuring RT activity twice a week post infection. Culture supernatants from virus-free CEM were tested as a control (white circles, FIG. 1b).

The present invention is therefore drawn to an inhibitor of HIV replication, comprising a peptide or analog comprising a decapeptide, said decapeptide containing (from the N-terminus to the C-terminus) a basic amino acid in position 1, an acidic amino acid in positions 2 and 5, and a tryptophan in positions 4, 7, and 8.

By inhibition of HIV replication, it is meant an inhibition of the production of viral particles from infected cells. This inhibition may be measured by different means, in particular as described in Morris et al. (15, which is incorporated herein by reference in totality).

In particular, an inhibitor of HIV replication according to the present invention reduces the β-galactosidase activity measured from MAGIC-5 cells by at least 50%, more preferably 70%, the most preferably 90% in the conditions reported in the examples of the present invention.

In a preferred embodiment, the basic amino acid in position 1 is arginine, or more preferably lysine.

In another embodiment, the acidic amino acid in position 2 is glutamate (also named glutamic acid).

In another embodiment, the acidic amino acid in position 5 is glutamate.

In another embodiment, the amino acid in position 3 is chosen in the group consisting of threonine, isoleucine and valine, and is preferably threonine.

In another embodiment, the amino acid in position 6 is chosen in the group consisting of threonine, alanine and glutamine and is preferably threonine or alanine.

In another embodiment, the amino acid in position 9 is chosen in the group consisting of threonine, alanine, valine, isoleucine, methionine, and aspartate (also named aspartic acid), and is preferably threonine.

In another embodiment, the amino acid in position 10 is chosen in the group consisting of glutamate, aspartate and asparagine, and is preferably glutamate or aspartate, more preferably glutamate.

In a preferred embodiment, the inhibitor of the invention comprises a decapeptide containing (from the N-terminus to the C-terminus) a basic amino acid in position 1, an acidic amino acid in positions 2 and 5, and a tryptophan in positions 4, 7, and 8.

In another embodiment, the inhibitor of the invention is a decapeptide containing (from the N-terminus to the C-terminus) a basic amino acid in position 1, an acidic amino acid in positions 2 and 5, and a tryptophan in positions 4, 7, and 8.

The peptide or analog that can be used preferably covers the residues 389-407 of the HIV-RT, more preferably 395-404.

By peptide or analog, it is meant to understand a molecule comprising a series of amino acids, that can be natural or not, said molecule being linear or circular, and capable of being modified, by linkages such as glycosylation or branches of amino acids such as glutamylation on glutamate(s).

A peptide according to the present invention can be obtained by genetic engineering, after introduction of a DNA vector carrying a nucleic acid sequence coding for the peptide sequence into a host cell (procaryotic or eucaryotic cell, such as bacteria, yeast, mammalian cell), and producing the peptide within said host cell. Some induction systems allow the production of a large amount of peptide, and are techniques well known by the person skilled in the art.

The peptides or analogs according to the present invention can also be obtained by chemical synthesis, using one of the many known peptidic synthesis. One could cite the techniques using solid phases, total or partial, by fragment condensation, or a synthesis in classical solution.

The peptides or analogs of the invention may comprise non natural or modified amino acids. Among these non naturally occurring amino acid, one could cite without being limitative, ornithine, norleucine, norvaline, hydroxyproline, hydroxylysine, ethylglycine, ethylasparagine. A list of modified amino acids has been edited by the WIPO in the definition of the sequence norm ST 25.

The peptides or analogs according to the present invention can contain modifications of the amino acids that are found naturally or not, among them glycosylation.

The sequence of the peptides or analogs according to the present invention can also be modified, without modification of the biological activity (inhibition of HIV-RI replication, in particular through inhibition of HIV-RT dimerization), in particular to increase their solubility, preferably in aqueous solvents.

The peptides or analogs according to the invention may be modified in order to increase their stability in vitro and/or in vivo. For example, one can use D amino acids and/or block the N and/or C-termini of the peptides.

It is possible to replace some minor amino-acids to increase the stability or allow a better penetration of the peptide or analog in the cell.

It is to understand that the acceptable modifications to the peptides or analogs maintain the biological activity of said molecules, which is to inhibit HIV replication.

The process for the purification of peptides are known by the person skilled in the art. Recombinant peptides can be purified from lysates or cellular extracts, from the supernatant of the culture medium by techniques used individually or in combination.

The techniques that can be used to purify peptides prepared through a recombinant host or by chemical synthesis include fractionation, chromatography, immunoaffinity techniques, using monoclonal or polyclonal specific antibodies.

The inhibitor according to the present invention exhibits a better potency when it further comprises a vector allowing the penetration of the peptide or analog into a mammalian cell.

The person skilled in the art can design such a vector, which preferably is comprised in the group consisting of liposomes, polymeric protein-binding cations, proteins, peptides, micro- or nanoparticles.

In a preferred embodiment of the invention, the vector used to facilitate the penetration of the peptide in the inhibitor of the present invention comprises the peptide MPG (SEQ ID NO:2), the amphipatic sequence of peptide MPG (SEQ ID NO:3) or an analog thereof.

In a preferred embodiment of the invention, the vector used to facilitate the penetration of the peptide in the inhibitor of the present invention is the peptide MPG (SEQ ID NO:2), the amphipatic sequence of peptide MPG (SEQ ID NO:3) or an analog thereof.

In a preferred embodiment, the peptide and the vector in the inhibitor according to the present invention are in the form of a complex.

In another embodiment, the peptide and the vector in the inhibitor according to the present invention are linked by a covalent liaison.

In a very preferred embodiment, the inhibitor according to the invention is formed by a peptide comprising peptide p7 (SEQ ID NO:1) and peptide MPG (SEQ ID NO:2) or the amphipatic sequence of peptide MPG (SEQ ID NO:3), or analogs thereof.

In the most preferred embodiment, the inhibitor according to the invention is peptide p7++ (retroinhibase 1, SEQ ID NO:4), or an analog thereof.

The invention is also drawn to a pharmaceutical composition comprising an inhibitor of HIV replication according to the invention, and an appropriate excipient. Said compositions are preferably formulated for administration to mammals, in particular human beings. They are preferably formulated to be administrated by oral, sublingual, subcutaneous intramuscular, intravenous, transdermal, rectal way.

The pharmaceutical composition may be a tablet, a capsule, a powder, a pill, a suppository, a solution (injectable by a method as previously cited) or a suspension.

The excipient may be gelatin, starch, lactose, arabic gum, talc, or other known pharmaceutical vehicles. The tablets may be coated by sucrose, or other appropriate compounds.

The pharmaceutical composition according to the invention may be treated as to achieve a sustained or retarded activity, or for the release of a predetermined amount of inhibitor in a continuous way.

The capsule may be obtained by mixing the inhibitor with a diluent and pouring the mixture in soft or hard capsules.

A syrup may be obtained by mixing the inhibitor with an sweetener, an antiseptic, a tasting agent, and an appropriate colorant.

Powders or granules may contain the inhibitor mixed with dispersion agents, or wetting agents, optionally with tasting agents and/or sweeteners.

For rectal administration, suppositories may be prepared with binding agents, melting at rectal temperature, such as cocoa butter or polyethyleneglycols.

For injectable administration, one could use aqueous suspensions, saline isotonic solutions or sterile solutions that contains dispersions agents, and/or wetting agents pharmacologically compatibles.

The inhibitor may also be formulated as a microcapsule, with possibly one or more additive supports.

The examples in the present application show that the inhibitors of the invention are very potent against the replication of HIV strains in vitro. Furthermore, they are also very potent against both HIV-1 and HIV-2 strains, as well as against drug- and multidrug-resistant strains.

Therefore, the invention is also drawn to the use of an inhibitor, or a composition according to the invention, for the manufacture of a medicament to be used in the treatment of an HIV infected patient, whether HIV is a HIV-1, HIV-2, drug sensitive, drug-resistant or multidrug-resistant HIV virus.

It is foreseen that the medicament of the present invention will be used simultaneously or in combination with one or more other anti-HIV medicament(s). Indeed, the best current clinical results for limiting HIV infections are obtained by using multiple drugs at the same time. The invention presents a new therapeutic class of molecules to be used against HIV, and shall therefore be added to the current treatment regimens.

The other anti-HIV medicaments that can be used at the same time as the medicament or the inhibitor of the invention include protease inhibitors and inhibitors of the HIV-RT, such as nucleoside or non-nucleosides inhibitors.

It is also worth noting that the inhibitors according to the present invention are directed against conserved region of the HIV-RT, that is essential for the dimerization of the protein. Therefore, by using the inhibitor of the invention, one can prevent the dimerization of the HIV-RT, which may prevent the reverse transcription of the virus RNA to DNA, and its integration within the genome.

Furthermore, the inhibitors and compositions of the invention are advantageous in that they target a conserved region of the virus genome, that is probably not very prone to mutations, as it is essential for the dimerization of the HIV-RT protein. It is therefore expected that there will be less resistant strains to the inhibitors of the invention than with other inhibitors of HIV-RT, such as nucleoside analogs.

The inhibitors of the present invention show an inhibition of virus replication for concentrations in the range of $10^{-7}$ or $10^{-8}$ M in vitro, that is lower than the concentration needed for AZT. Furthermore, cell toxicity is only observed for inhibitor concentration 10,000 times higher.

It is therefore foreseen that the inhibitors or the composition according to the present invention will be administered at a dose that will allow them to be effective. Such a dose is said to be therapeutically effective, i.e. anti-virally effective, without a reduced toxicity.

According to the literature that reports on the use of peptides as therapeutic agents (40), the medicament of the invention may be administered at a dose of about 1 to 1000 mg/day, or more preferably at a dose of about 20 to 700 mg/day.

The invention is also drawn to a method for treating or inhibiting an HIV infection comprising administering to a human in need thereof a therapeutically effective (anti-virally effective) amount of an inhibitor, or a composition according to the invention, optionally in combination with a therapeutically effective amount of one or more other anti-HIV medicament(s) (such as nucleosides or non-nucleosides inhibitors of the reverse transcriptase, protease inhibitors).

The method is effective against HIV-1 or HIV-2, and particularly against drug- or multidrug-resistant HIV.

EXAMPLES

Example 1

Methods 1.1 Viruses

The HIV strains used in this study were already described: HIV-1 BRU (28), HIV-2 ROD (29), HIV-1 ELI (30), HIV-2EHO (31,32), HIV-1 NDK (33), HIV-1 RF (34), HIV-1 SF2 (35), nevirapine-resistant HIV-1N119 (20), HIV-1 RTMC (21), HIV-1 RTMF (18), HIV-1 74V (36), and HIV-1 RTMDR1 (24). These viruses were propagated in CEM cells (a CD4+/CXCR4+ human T-cell line).

1.2. Cells

The CD4+, CXCR4+ lymphoblastoid CEM cell line was purchased from the American Type Culture Collection (CCRF-CEM, ATCC # CCL 119, Catalogue of cell lines and hybridomas, ATCC, Bethesda, Md.). CEM cells were cultured in RPMI 1640 medium containing 1% penicillin-streptomycin (PS) antibiotic mixture, 1% glutamax (Gibco-BRL, Eragny, France) and 10% FCS (Gibco), to a density of $5 \times 10^5$ cells/ml in a 5% $CO_2$ atmosphere. The HeLa-LTR-βgal indicator cell line (37) stably transfected with CD4 and CCR5 (MAGIC-5) cells was previously described (38), were grown in DMEM containing 1% PS, 1% glutamax, 1 mg/ml G418, and 10% FCS.

1.3. Peptides

Peptides (p7 (SEQ ID NO:1), p237 (SEQ ID NO:5), MPG (SEQ ID NO:2), p7++ (SEQ ID NO:4), and p7+ (SEQ ID NO:6)) were synthesized by solid phase peptide synthesis using aminoethyldithio-2-isobutyric acid-expensin resin with a 9050 Pepsynthetizer (Millipore, UK) according to the Fmoc (N-(9-fluorenyl)methoxycarbonyl)/tert-butyl method, purified by semi-preparative HPLC and identified by electrospray mass spectrometry and amino acid analysis. In some case, to increase their stability, the peptides were acetylated at the N terminus and linked to a cysteamide group at the C-terminal part as previously described (14).

1.4. Formation of p7/MPG Complex

Peptide p7 (SEQ ID NO:1) and MPG (SEQ ID NO:2) were mixed, and peptide p7 binds to MPG (probably the hydrophobic domain), with saturation taking place for a concentration of p7 about 20-fold lower than of MPG. From the $K_d$ and the saturation concentration, the ration was estimated to 30 molecules of MPG for one molecule of p7. The MPG/p7 complex was further assessed as a complex of p7-MPG at a 1/20 ratio (15, incorporated herein by reference in its totality).

1.5. Infection of Cells

RI activity assay. CEM cells were incubated for 30 mm at 4° C. with 100 µl of stock HIV preparation corresponding to 1000×50% tissue culture infective dose ($TCID_{50}$)/ml, then cells were washed five times and cultured at $5 \times 10^5$ cell/ml in 24-well microplates in the presence or absence of MPG/p7 (at $10^{-8}$ and $10^{-7}$ M) or AZT (AZT was purchased from Boehringer Mannheim, Germany) additive. Viral production was monitored twice a week by measuring reverse transcriptase activity in 1 ml of cell-free supernatant as previously described (39).

β-gal activity assay. MAGIC-5 cells expressing the β-gal reporter gene cloned downstream of the HIV-1 LTR promoter were plated in 24-well plates at $5 \times 10^{-5}$ cells/ml and incubated with 50 µl of stock HIV preparation corresponding to 1000× 50% tissue culture infective dose ($TCID_{50}$)/ml in the presence or absence of MPG/p7 (at $10^{-8}$ and $10^{-7}$M) or AZT additive. After 3 days in culture, cells were lysed and β-gal activity was determined by incubating 200 µl of total cellular extracts for 1 h at 37° C. in 1.5 ml buffer containing 80 mM $NA_2HPO_4$, 10 mM $MgCl_2$, 1 mM 2 ME and 6 mM o-nitrophenyl β-D-galactopyranoside (ONPG). β-gal activity was evaluated by measuring absorbance at 410 nm.

Example 2

Inhibition of HIV-1 and HIV-2 Isolates Replication in CEM Cells by MIPG/p7 Complex MPG/p7 was previously shown to inhibit HIV-1BRU RT dimerization in vitro and HIV-1BRU replication in CEM cell culture (15, incorporated herein by reference). The susceptibility of two reference strains of laboratory-adapted HIV-1 and HIV-2 to MPG/p7 was first determined.

A representative experiment of inhibition of virus production (HIV-1 BRU and HIV-2ROD) in infected CEM cells treated with MPG/p7 ($10^{-6}$ M), a 15-mer control peptide 237 ($10^{-6}$ M) (SEQ ID NO:5), or AZT ($10^{-5}$M), is shown in FIG. 1. RT activity monitored in cell free culture supernatant of infected cells from day 3 to day 17 after virus exposure, indicated that MPG/p7 at concentrations above $10^{-8}$ M, totally inhibits HIV-1BRU replication during the 17 days of incubation whereas RT activity observed at the end of culture in samples treated at concentration of $10^{-9}$ M revealed a very slow virus propagation that was undetected at earlier timepoints. Only a 3-days delay in HIV-1 replication was found at a concentration of $10^{-10}$ M of MPG/p7.

Under similar experimental conditions HIV-2ROD propagation was strongly delayed at concentrations of MPG/p7 above $10^{-7}$ M, whereas a 3-days delay in HIV-2 replication was observed using a concentration of $10^{-9}$ M of MPG/p7.

This result was confirmed by monitoring the expression of HIV-1 antigen by $p24^{gag}$ antigen capture assay on day 17 post infection (data not shown).

Example 3

Inhibition of HIV-1 and HIV-2 Isolates Replication in MAGIC5 Cells by MPG/p7 Complex The pattern of reactivity of MPG/p7 using several isolates from different clades of HIV-1 and HIV-2 isolates (see Table 1) was next determined.

The efficiency of MPG/p7 monitored using the previously described MAGIC5 transfectant cells that express surface CD4, CXCR4 and CCR5 receptors and contain a reporter gene under control of an HIV-1 promoter that can be induced upon infection of the cells. This assay was chosen because it gives a result within 72 h and requires much less peptide in each experiment than classical infection assays.

All strains tested were found to be susceptible to MPG/p7 at concentrations of $10^{-8}$ M (FIG. 2). This included X4 and R5/X4 strains of HIV-1 from clades B and D and HIV-2 clades A and B.

Although only HIV-1 clades B and D and HIV-2 clades A and B isolates were tested, it can be assumed that the 7 isolates that were used in the present study are representative of the different sequences that can be encountered within HIV-1 clades A, B, C, D, F, G, H, O and HIV-2 clades A and B.

Indeed, comparisons of the sequence of residues 395-404 of HIV-1 $BH_{10}RT$ (KETWETWWTE, SEQ ID NO:1) to the corresponding sequences available from the Los Alamos data base (9) (Table 1) reveals that the major substitutions observed between the consensus B and the other clades of HIV-1 are found in one of the HIV-1 B or D, or HIV-2 viruses tested.

For example, the HIV-1 Glade C (see consensus C sequence) that is most predominant in India and causes more than 70% of infections in southern Africa and 96% in northern Africa shows a $T_{404}A$ substitution also encountered in HIV-1 RF and HIV-1 NDK and an $E_{404}D$ substitution also encountered in HIV-2 EHO.

Therefore, in most cases substitutions do not alter the character of the residues, confirming that this region is highly conserved in HIVs.

These observations suggest that irrespectively of type, Glade and geographic origin, all human lentiviruses containing a decapeptide containing (from the N-terminus to the C-terminus) a basic amino acid in position 1, an acidic amino acid in positions 2 and 5, and a tryptophan in positions 4, 7, and 8 at the interface of the connecting subdomains of the p66 and p51 subunits can potentially be inhibited by MPG/p7.

Example 4

Crystallographic Analysis of the HIV-RT

The crystallographic structure of HIV-1 RT, reveals that the residues 395-404 are involved in the p66/p51 interface contacts and are essential in the stabilization of both the connection subdomain.

Secondary structure predictions and molecular modeling suggest that in all the isolates these residues are folded into an α-helix, as observed in the X-ray structure of HIV-1 (16,17).

In both subunits, the highly conserved Trp residues, $Trp_{398}$, $Trp_{401}$ and $Trp_{402}$ form a cluster of aromatic residues together with $Tyr_{405}$, $Trp_{410}$, and $Phe_{416}$ which stabilizes the dimer interface by intra- and inter-subunit contacts. In p51 the hydrohobic cluster involves other contacts which maintains the conformation of the palm domain of p51 ($Trp_{24}$, $Phe_{61}$, $Leu_{368}$, $Leu_{391}$, $Val_{372}$) and the thumb-domain of p66 ($Arg_{356}$, $Arg_{358}$, $Gln_{373}$). In p66, additional contacts are made with the RNase-H domain ($Val_{423}$, $Leu_{425}$).

Analysis of the amino acid substitutions indicated that whatever the sequence mentioned in Table 1, the property of the residues is conserved in order to maintain the organization of the hydrophobic pocket and the α-helix conformation.

Substitution $K_{395}R$ or $E_{399}D$ retains the basic characteristic, essential for helix stability and interactions with $Trp_{24}$, $Phe_{416}$ and $Trp_{414}$.

Substitution $E_{396}D$ keep the acidic property essential for the interaction with residues $Gln_{394}$ in p51 and the two $Arg_{356}$ and $Arg_{358}$ in p66.

$Thr_{397}$ is conserved in all of the consensus sequences, excepted in HIV-2 consensus A, in both subunits this residue is surrounded by hydrophobic residues, which cannot be altered when replaced by isoleucine or valine.

$Thr_{400}$ is one of the most variable residue of this motif, therefore none of the substitution alters the organization of the aromatic cluster.

Moreover, the substitution $T_{400}Q$ observed in all HIV-2 consensus increases interaction between p51 and p66 subunits and may explain the higher stability of HIV-2 $RT^{11}$.

Taken together, these data indicate that MPG/p7 inhibits a wide range of HIVs. Based on these results we conclude that the integrity of the aromatic cluster which is essential for dimer formation as well as for the structural integrity of both subunits, is conserved in all of the isolates described in Table 1. This explains why a drug like p7, which targets the aromatic cluster prevents the dimer formation of all of these isolates.

Example 5

Susceptibility of Anti-RT Drug Resistant HIV-1 Strains to MPG/p7

The phenotypic identification of drug-resistant HIV-1 emerging during unsuccessful antiretroviral therapy has enable the definition of drug resistant genotypes of HIV-1.

Several mutations in RT are consistently in association with resistance to one or more anti-RT drugs. The growing number of reports documenting mutations which confer resistance to both nucleoside and non-nucleoside RT inhibitors indicates that one of the first selection criteria that a new antiviral compound targeting RT should meet, is its capacity to inhibit anti-RT drug resistant HIV-1 strains.

According to the compilation of mutations in HIV RT published by the Los Alamos National Laboratory (9), there are at least 45 amino acid residues in RT for which mutations result in a significant change in the virus susceptibility to one or more anti-RT drugs.

Interestingly, and to the best of our knowledge, there is actually no mutation reported affecting the residues of HIV-1 RT that are target for MPG/p7. Moreover, that mutation of $Trp_{398}$ and $Trp_{410}$ (HIV-1 BH10) strongly affected the stability of the dimeric form of HIV-1 RT in vitro (Morris and Divita, unpublished data), strengthens the hypothesis that mutations occurring in this region may affect RT dimerization thereby disabling viral replication.

To determine whether mutant HIV-1s that resist to both nucleoside and/or nonnucleoside RT inhibitors are sensitive to MPG/p7, five reference strains of anti-RT drug resistant HIV-1 were assayed for susceptibility to MPG/p7.

Table 2 summarizes the characteristics of RT drug resistant phenotype of these viruses, namely HIV-1 RTMF, HIV-1 RTMC, HIV-1 74V, HIV-1 N119 and HIV-1 RTMDR1, and the type of mutation conferring these phenotypes.

The different escape mutant viruses studied turned to be sensitive to MPG/p7 treatment (FIG. 3). It is however worth noting that the concentration of MPG/p7 required to inhibit HIV-1 RTMC and HIV-1 RTMDR1 (FIG. 3c and f) was higher than that required to block the other viruses. For example, $10^{-6}$ M of MPG/p7 was required for completely inhibit HIV-1 RTMC (data not shown).

The fact that the sensitivity to zidovudine of HIV-1 RTMC and HIV-1 RTMF escape mutant strains was very similar in the present experiment and in the experiment previously reported by Larder and co-workers (18), validated the observations relatively to MPG/p7 effect on the different escape mutant viruses.

Example 6

Inhibition of HIV Replication by Peptide $D^7$++

In order to further study the properties of peptide p7, chimeric peptides having the transmembranaire transport properties of MPG (amhipathic sequence) and anti HIV-RT properties of p7 were designed and synthesized.

Peptide p'7++ (SEQ ID NO:4) and p7+ (SEQ ID NO:6) were used on MAGIC-5 cells, infected with the ROD (HIV-2) and BRU (HIV-1) strains.

FIG. 4 shows that peptide p7++ (retroinhibase 1) exhibits the same activity than the MPG-p7 complex at about the same concentration.

The use of peptide p7++ on cells infected by drug-resistant viruses demonstrates that this peptide is also capable to inhibit the replication of such strains (FIG. 4).

TABLE 1

Table 1 Amino acid alignment with the p7 sequence of BH10 strain

| Type | Strain | Clade | Country of origin | Sequence | | SEQ ID NO |
|---|---|---|---|---|---|---|
| HIV-1 | | | | 395 | 404 | |
| | BH10 | | | KETWETWWTE (p7) | | 1 |
| | BRU | B | France | KETWETWWTE | | 1 |
| | RF | B | Haiti/USA | KETWEAWWTE | | 7 |
| | SF2 | B | USA | KETWEAWWME | | 8 |
| | NDK | D | Zaire | KETWETWWIE | | 9 |
| | ELI | D | Zaire | KETWETWWAE | | 10 |

TABLE 1-continued

Table 1 Amino acid alignment with the p7 sequence of BH10 strain

| Type | Strain | Clade | Country of origin | Sequence | SEQ ID NO |
|---|---|---|---|---|---|
| HIV-2 | | | | | |
| | ROD | A | Cape Verde | REIWEQWWDN | 11 |
| | EHO | B | Ivory Coast | RETWDQWWTD | 12 |
| HIV-1 | | | | 395 (p7) 404 KETWETWWTE | 1 |
| Consensus | | A | | KETWE$_{T/A}$WWT$_{E/D}$ | 13 |
| Consensus | | B | | KETWE$_{T/A}$WWME | 14 |
| Consensus | | C | | KETWEAWWTD | 15 |
| Consensus | | D | | KETWE$_{T/A}$WWX$_{E/D}$ (X = T/$_A$/$_{T/I}$) | 16 |
| Consensus | | F | | KETWDTWWTE | 17 |
| Consensus | | G | | KETWEVWWTE | 18 |
| Consensus | | H | | KETWETWWTE | 1 |
| Consensus | | O | | RETWETWWAD | 19 |
| HIV-2 | | | | | |
| Consensus | | A | | R$_{E/D}$ZWEQWWD$_{N/D}$ (Z = T/$_{T/I}$) | 20 |
| Consensus | | B | | RETWDQWWTD | 21 |

Sequences are from ref. 9

TABLE 2

Main characteristics of anti-RT drug resistant HIV-1 isolates

| Strain | RT Genotyping | Phenotype |
|---|---|---|
| HIV-1 RTMF | 215Y | AZT-resistant |
| HIV-1 RTMC | 67N, 70R, 215F, 219Q | AZT-resistant |
| HIV-1 74V | 74V | resistant ddI and ddC |
| HIV-1 N119 | 181C | resistant to nevapirine and non nucleoside RT inhibitors |
| HIV-1 RTMDR1 | 41L, 74V, 106A, 215Y | resistant to AZT, ddI, nevapirine, non nucleoside RT inhibitors |

Viruses phenotype and reverse transcriptase genotype are adapted from refs. 18, 20, 21, 23, and 36. HIV-1 RTMF, RTMC, 74V, RTMDR1, and N119 viruses utilize CXCR4 (some isolates are R5X4 dual tropic strains).

REFERENCES

1. Tantillo, C. et al. Locations of anti-AIDS drug binding sites and resistance mutations in the three-dimensional structure of HIV-1 reverse transcriptase. Implications for mechanisms of drug inhibition and resistance. *J. Mol. Biol.* 243, 369-387 (1994).
2. Volberding, P. The need for additional options in the treatment of human immunodeficiency virus infection. *J. Inf. Dis.* 171 (Suppl. 2), 150-154 (1995).
3. Preston, B. D., Poiesz, B. J. & Loeb L. A. Fidelity of HIV-1 reverse transcriptase. *Science* 242, 1168-1171 (1988).
4. Roberts, J. D., Bebenek, K. & Kunkel, T. A. The accuracy of reverse transcriptase from HIV-1. *Science* 242, 1171-1173 (1988).
5. Richman, D. D. Antiretroviral drug resistance: mechanisms, pathogenesis, clinical significance. *Adv. Exp. Med. Biol.* 394, 383-395 (1996).
6. Hirschel, B. & Opravil, M. The year in review: antiretroviral treatment. *AIDS* 13 (Suppl. A), 177-187 (1999).
7. Boucher, C. A. et al. Ordered appearance of zidovudine resistant mutations during treatment of 18 human immunodeficiency virus-positive subjects. *J. Inf Dis.* 165, 105-110 (1992).
8. Goudsmit, J., de Ronde, A., de Rooij, E. & de Boer, R. Broad spectrum of in vivo fitness of human immunodeficiency virus type 1 subpopulations differing at reverse transcriptase codons 41 and 215. *J. Virol.* 71, 4479-4484 (1997).
9. Korber, B. et al. Human retroviruses and AIDS. A compilation and analysis of nucleic acid and amino acid sequences. Los Alamos National Laboratory, Los Alamos, New Mexico (1998).
10. Restle, T., Muller, B. & Goody, R. S. Dimerization of human immunodeficiency virus type 1 reverse transcriptase. A target for chemotherapeutic intervention. *J. Biol. Chem.* 265, 8986-8988 (1990).
11. Divita, G., Rittinger, K., Geourjon, C., Deleage, G. & Goody, R. S. Dimerization kinetics of HIV-1 and HIV-2 reverse transcriptase: a two step process. *J. Mol. Biol.* 245, 508-521, (1995).
12. Divita, G., Restle, T., Goody, R. S., Chemann, J.-C. & Baillon, J. C. Inhibition of human immunodeficiency virus type 1 reverse transcriptase dimerization using synthetic peptides derived from the connection domain. *J. Biol. Chem.* 269, 13080-13083 (1994).
13. Divita, G., Baillon, J. G., Rittinger, K., Chemann, J.-C. & Goody, R. S. Interface peptides as structure-based human immunodeficiency virus reverse transcriptase inhibitors. *J. Biol. Chem.* 270, 28642-28646 (1995).
14. Morris, M., Vidal, P., Chaloin, L., Heitz, F. & Divita, G. A new peptide vector for efficient delivery of oligonucleotides into mammalian cells. *Nuc. Acids Res.* 25, 2730-2736 (1997).
15. Morris, M. et al. A new potent HIV-1 reverse transcriptase inhibitor. *J. Biol. Chem.* 274, 24941-24946 (1999).
16. Jacobo-Molina, A. et al. Crystal structure of human immunodeficiency virus type I reverse transcriptase complexed with double stranded DNA at 3.0 A resolution shows bent DNA. *Proc. Natl. Acad. Sci.* USA 90, 6320-6324 (1993).
17. Kohlstaedt, L. A., Wang, J., Friedman, J. M., Rice, P. A., & Steitz, T. A. Crystal structure at 3.5 A resolution of HIV-1 reverse transcnptase complexed with an inhibitor. *Science* 256, 1783-1790 (1992).
18. Larder, B. A., Kellam, P. & Kemps, S. D. Zidovudine resistantce predicted by direct detection of mutations in DNA from HIV-infected lymphocytes. *AIDS* 5, 137-144 (1991).
19. Richman, D. et al. BI-RG-587 is active against zidovudine-resistant human immunodeficiency virus type 1 and synergistic with zidovudine. *Antimicrob. Agents Chemother.* 35, 305-308 (1991).
20. Richman, D. et al. Human inimunodeficiency virus type 1 mutants resist to nonnucleside inhibitors of reverse transcriptase arise in tissue culture. *Proc. Natl. Acad. Sci., USA.* 88, 11241-11245 (1991).
21. Larder, B. A. & Kemps, S. D. Multiple mutations in HIV-1 reverse transcriptase confer high-level resistance to zidovudine (AZT). *Science* 246, 1155-1158 (1989).
22. Nunberg, J. H. et al. Viral resistance to human itnmunodeficiency virus type 1-specific pyridinone reverse transcriptase inhibitors. *J. Virol.* 65, 4887-4892 (1991).
23. Gao, Q., Gu, Z., Parniak, M. A., Li, X. & Wainberg, M. A. In vitro selection of variants of human immunodeficiency virus type 1 resistant to 3'-azido-3' deoxythymidine and 2',3'-dideoxyinosine. *J. Virol.* 66, 12-19 (1992).
24. Larder, B. A., Kellam, P. & Kemps, S. D. Convergent combination therapy can select viable multidrug-resistant HIV-1 in vitro. *Nature* 365, 451-453 (1993).

25. Tachedjian, G., Aroson, H.-E., & Goff, S. P. Analysis of mutations and repressors affecting interactions between the subunits of the HIV-1 reverse transcriptase. *Proc. Natl. Acad Sd. USA* 97, 6334-6339 (2000).

26. Sluis-Cremer, N., Dmitrienko, O.1., Balzarini, J., Camarasa, M. J., & Parniak, M. A. Human immunodeficiency virus type 1 reverse transcriptase dimer destabilization by 1-[Spiro[4"-amino-2",2"-dioxo-1",2"-oxathiole-5",3'[2', 5'-bis-O-(tert-butyldimethylsilyl)-beta-D-ribofuranosyl]]]-3-ethylthymine. *Biochemistry* 39, 1427-1433 (2000).

27. Grossman, Z. et al. Ongoing HIV dissemination during HAART. *Nature Med.* 5, 1099-1104 (1999).

28. Barré-Sinoussi, F. et al. Isolation of a T-lymphotropic retrovirus from a patient at risk for acquired immune deficiency syndrome (AIDS). Science 220:868-871 (1983).

29. Clavel, F. et al. Isolation of a new human retrovirus from west Africa patients with AIDS. *Science* 223, 343-346 (1986).

30. Alizon, M., Wain-Hobson, S., Montagnier, L. & Sonigo, P. Genetic variability of the AIDS virus: nucleotide sequence analysis of two isolates from African patients. *Cell* 46, 63-74 (1986).

31. Rey-Cuille, M. A. et al. HIV-2 EHO isolate has a divergent envelope gene and induces single cell killing by apoptosis. *Virology* 202, 471-476 (1994).

32. Galabru, J., Rey-Cuille, M. A. & Hovanessian, A. Nucleotide sequence of HIV-2 EHO genome, a divergent HIV-2 isolate. AIDS Res. Hum. Retroviruses. 11, 873-874 (1995).

33. Ellrodt, A. et al. Isolation of human T-lymphotropic retrovirus (LAV) from Zairan married couple, one with AIDS, one with prodomes. *Lancet* i:1383-1385 (1984).

34. Popovic, M., Sarngadharan, M. G., Read, E. & Gallo, R. C. Detection, isolation, and continuous production of cytopathic retroviruses (HTLV-III) from patients with AIDS and pre-AJDS. *Science* 224, 497-500 (1984).

35. Levy, J. A. et al. Isolation of lymphocytopathic retrovirus from San Francisco patients with AIDS. *Science* 225, 840-842 (1984).

36. St. Clair, M. H. et al. Resistance to ddI and sensitivity to AZT induced by a mutation in HIV-1 reverse transcriptase. *Science* 253, 1557-1559 (1991).

37. Kimpton & Emerman. Detection of replication-competent and pseudotyped human immunodeficiency virus with a sensitive cell line on the basis of activation of an integrated beta-galactosidase gene. *J. Virol.* 66, 2232-2239 (1992).

38. Mochizuki, N. et al. An infectious DNA clone of HIV subtype C. AIDS *Res. Hum. Retroviruses* 15, 1321-1324 (1999).

39. Rey, M. A. et al. Characterization of the RNA dependent DNA polymerase of a new human T-lymphotropic retrovirus (LAV). *Biochem. Biophys. Res. Commun.* 121, 126-133 (1984).

40. Briant and Devaux. Bioactive CD4 ligands as pre- and/or postbinding inhibitors of HIV-1. In Advances in Pharmacology, Vol 48 (ed., K.-T. Jeang), pp. 373-407, (2000).

What is claimed is:

1. An inhibitor of HIV replication, comprising an antiviral peptide, wherein:

the antiviral peptide consists of a decapeptide containing (from the N-terminus to the C-terminus) a basic amino acid at position 1; an acidic amino acid at positions 2 and 5; a tryptophan at positions 4, 7, and 8; a threonine, isoleucine or valine at position 3; a threonine, alanine, or glutamine at position 6; a threonine, alanine, valine, isoleucine, methionine, or aspartate at position 9; and a glutamate, aspartate or asparagine at position 10;

the decapeptide inhibits the dimerization of HIV reverse transcriptase; and the decapeptide is not KETWETWWTE (SEQ ID NO: 1).

2. The inhibitor of claim 1, wherein the basic amino acid at position 1 is lysine or arginine.

3. The inhibitor of claim 1, wherein the acidic amino acid at position 2 is glutamate.

4. The inhibitor of claim 1, wherein the amino acid at position 5 is glutamate.

5. The inhibitor of claim 1, further comprising a pharmaceutically acceptable excipient.

6. The inhibitor of claim 1, further comprising a vector that allows penetration of the antiviral peptide into a mammalian cell.

7. The inhibitor of claim 6, wherein the vector is selected from the group consisting of: a liposome, a polymeric protein-binding cation, a protein, a peptide, a microparticle, and a nonoparticle.

8. The inhibitor of claim 7, wherein the vector is a peptide.

9. The inhibitor of claim 8, wherein the peptide is an MPG peptidyl carrier.

10. The inhibitor of claim 9, wherein the MPG peptidyl carrier comprises SEQ ID NO: 2 or SEQ ID NO: 3.

11. The inhibitor of claim 9, wherein the MPG peptidyl carrier and the antiviral peptide are in the form of a complex.

12. The inhibitor of claim 11, wherein the complex comprises the MPG peptidyl carrier and the antiviral peptide at a ratio of 20 molecules of the MPG peptidyl carrier for 1 molecule of the antiviral peptide.

13. An inhibitor of HIV replication comprising a chimeric peptide, wherein the chimeric peptide comprises:

(a) a decapeptide containing (from the N-terminus to the C-terminus) a basic amino acid at position 1; an acidic amino acid at positions 2 and 5; a tryptophan at positions 4, 7, and 8; a threonine, isoleucine or valine at position 3; a threonine, alanine, or glutamine at position 6; a threonine, alanine, valine, isoleucine, methionine, or aspartate at position 9; and a glutamate, aspartate or asparagine at position 10; wherein the decapeptide inhibits the dimerization of HIV reverse transcriptase, and (b) an MPG peptidyl carrier peptide.

14. The inhibitor of claim 13, wherein the basic amino acid at position 1 is lysine or arginine.

15. The inhibitor of claim 13, wherein the acidic amino acid at position 2 is glutamate.

16. The inhibitor of claim 13, wherein the amino acid at position 5 is glutamate.

17. The inhibitor of claim 13, further comprising a pharmaceutically acceptable excipient.

18. The inhibitor of claim 13, wherein the MPG peptidyl carrier peptide is SEQ ID NO: 2 or SEQ ID NO: 3.

19. The inhibitor of claim 13, wherein the decapeptide is SEQ ID NO: 1.

20. The inhibitor of claim 13, wherein the chimeric peptide is SEQ ID NO: 4.

21. The inhibitor of claim 13, wherein the chimeric peptide is SEQ ID NO: 6.

* * * * *

```
                       SEQUENCE LISTING

<160> NUMBER OF SEQ ID NOS: 21

<210> SEQ ID NO 1
<211> LENGTH: 10
<212> TYPE: PRT
<213> ORGANISM: HIV
<220> FEATURE:
<223> OTHER INFORMATION: Residues 395-404 of HIV-1 BH10RT

<400> SEQUENCE: 1

Lys Glu Thr Trp Glu Thr Trp Trp Thr Glu
1               5                   10

<210> SEQ ID NO 2
<211> LENGTH: 27
<212> TYPE: PRT
<213> ORGANISM: Artificial Sequence
<220> FEATURE:
<223> OTHER INFORMATION: Peptide MPG

<400> SEQUENCE: 2

Gly Ala Leu Phe Leu Gly Phe Leu Gly Ala Ala Gly Ser Thr Met Gly
1               5                   10                  15

Ala Trp Ser Gln Pro Lys Ser Lys Arg Lys Val
            20                  25

<210> SEQ ID NO 3
<211> LENGTH: 6
<212> TYPE: PRT
<213> ORGANISM: Artificial Sequence
<220> FEATURE:
<223> OTHER INFORMATION: Amphipatic sequence of peptide MPG

<400> SEQUENCE: 3
```

-continued

Gly Phe Leu Gly Ala Ala
1               5

<210> SEQ ID NO 4
<211> LENGTH: 25
<212> TYPE: PRT
<213> ORGANISM: Artificial Sequence
<220> FEATURE:
<223> OTHER INFORMATION: Retroinhibase 1, peptide p7++

<400> SEQUENCE: 4

Gly Phe Leu Gly Ala Ala Gly Ser Thr Met Gly Ala Trp Ser Gln Lys
1               5                   10                  15

Glu Thr Trp Glu Thr Trp Trp Thr Glu
            20                  25

<210> SEQ ID NO 5
<211> LENGTH: 15
<212> TYPE: PRT
<213> ORGANISM: HIV
<220> FEATURE:
<223> OTHER INFORMATION: Peptide p237

<400> SEQUENCE: 5

Arg Gly Thr Lys Ala Leu Thr Glu Val Ile Pro Leu Thr Glu Asp
1               5                   10                  15

<210> SEQ ID NO 6
<211> LENGTH: 21
<212> TYPE: PRT
<213> ORGANISM: Artificial Sequence
<220> FEATURE:
<223> OTHER INFORMATION: Peptide p7+

<400> SEQUENCE: 6

Gly Ala Leu Phe Leu Gly Phe Leu Gly Ala Ala Lys Glu Thr Trp Glu
1               5                   10                  15

Thr Trp Trp Thr Glu
            20

<210> SEQ ID NO 7
<211> LENGTH: 10
<212> TYPE: PRT
<213> ORGANISM: HIV-1

<400> SEQUENCE: 7

Lys Glu Thr Trp Glu Ala Trp Trp Thr Glu
1               5                   10

<210> SEQ ID NO 8
<211> LENGTH: 10
<212> TYPE: PRT
<213> ORGANISM: HIV-1

<400> SEQUENCE: 8

Lys Glu Thr Trp Glu Ala Trp Trp Met Glu
1               5                   10

<210> SEQ ID NO 9
<211> LENGTH: 10
<212> TYPE: PRT
<213> ORGANISM: HIV-1

<400> SEQUENCE: 9

```
Lys Glu Thr Trp Glu Thr Trp Ile Glu
1               5                   10

<210> SEQ ID NO 10
<211> LENGTH: 10
<212> TYPE: PRT
<213> ORGANISM: HIV-1

<400> SEQUENCE: 10

Lys Glu Thr Trp Glu Thr Trp Ala Glu
1               5                   10

<210> SEQ ID NO 11
<211> LENGTH: 10
<212> TYPE: PRT
<213> ORGANISM: HIV-2

<400> SEQUENCE: 11

Arg Glu Ile Trp Glu Gln Trp Trp Asp Asn
1               5                   10

<210> SEQ ID NO 12
<211> LENGTH: 10
<212> TYPE: PRT
<213> ORGANISM: HIV-2

<400> SEQUENCE: 12

Arg Glu Thr Trp Asp Gln Trp Trp Thr Asp
1               5                   10

<210> SEQ ID NO 13
<211> LENGTH: 10
<212> TYPE: PRT
<213> ORGANISM: HIV-1
<220> FEATURE:
<221> NAME/KEY: VARIANT
<222> LOCATION: 6
<223> OTHER INFORMATION: Xaa = Thr or Ala
<220> FEATURE:
<221> NAME/KEY: VARIANT
<222> LOCATION: 10
<223> OTHER INFORMATION: Xaa = Glu or Asp

<400> SEQUENCE: 13

Lys Glu Thr Trp Glu Xaa Trp Trp Thr Xaa
1               5                   10

<210> SEQ ID NO 14
<211> LENGTH: 10
<212> TYPE: PRT
<213> ORGANISM: HIV-1
<220> FEATURE:
<221> NAME/KEY: VARIANT
<222> LOCATION: 6
<223> OTHER INFORMATION: Xaa = Thr or Ala

<400> SEQUENCE: 14

Lys Glu Thr Trp Glu Xaa Trp Trp Met Glu
1               5                   10

<210> SEQ ID NO 15
<211> LENGTH: 10
<212> TYPE: PRT
<213> ORGANISM: HIV-1

<400> SEQUENCE: 15

Lys Glu Thr Trp Glu Ala Trp Trp Thr Asp
```

-continued

```
<210> SEQ ID NO 16
<211> LENGTH: 10
<212> TYPE: PRT
<213> ORGANISM: HIV-1
<220> FEATURE:
<221> NAME/KEY: VARIANT
<222> LOCATION: 6
<223> OTHER INFORMATION: Xaa = Thr or Ala
<220> FEATURE:
<221> NAME/KEY: VARIANT
<222> LOCATION: 9
<223> OTHER INFORMATION: Xaa = Thr, Ala, Val or Ile
<220> FEATURE:
<221> NAME/KEY: VARIANT
<222> LOCATION: 10
<223> OTHER INFORMATION: Xaa = Glu or Asp

<400> SEQUENCE: 16

Lys Glu Thr Trp Glu Xaa Trp Trp Xaa Xaa
 1               5                  10

<210> SEQ ID NO 17
<211> LENGTH: 10
<212> TYPE: PRT
<213> ORGANISM: HIV-1

<400> SEQUENCE: 17

Lys Glu Thr Trp Asp Thr Trp Trp Thr Glu
 1               5                  10

<210> SEQ ID NO 18
<211> LENGTH: 10
<212> TYPE: PRT
<213> ORGANISM: HIV-1

<400> SEQUENCE: 18

Lys Glu Thr Trp Glu Val Trp Trp Thr Glu
 1               5                  10

<210> SEQ ID NO 19
<211> LENGTH: 10
<212> TYPE: PRT
<213> ORGANISM: HIV-1

<400> SEQUENCE: 19

Arg Glu Thr Trp Glu Thr Trp Trp Ala Asp
 1               5                  10

<210> SEQ ID NO 20
<211> LENGTH: 10
<212> TYPE: PRT
<213> ORGANISM: HIV-2
<220> FEATURE:
<221> NAME/KEY: VARIANT
<222> LOCATION: 2
<223> OTHER INFORMATION: Xaa = Glu or Asp
<220> FEATURE:
<221> NAME/KEY: VARIANT
<222> LOCATION: 3
<223> OTHER INFORMATION: Xaa = Thr, Val or Ile
<220> FEATURE:
<221> NAME/KEY: VARIANT
<222> LOCATION: 10
<223> OTHER INFORMATION: Xaa = Asn or Asp
```

```
<400> SEQUENCE: 20

Arg Xaa Xaa Trp Glu Gln Trp Trp Asp Xaa
 1               5                  10

<210> SEQ ID NO 21
<211> LENGTH: 10
<212> TYPE: PRT
<213> ORGANISM: Artificial Sequence
<220> FEATURE:
<223> OTHER INFORMATION: HIV-1

<400> SEQUENCE: 21

Arg Glu Thr Trp Asp Gln Trp Trp Thr Asp
 1               5                  10
```